United States Patent
Takahashi

(10) Patent No.: US 6,345,534 B1
(45) Date of Patent: Feb. 12, 2002

(54) NONDESTRUCTIVE FATIGUE TEST METHOD FOR FERROMAGNETIC CONSTRUCTION MATERIALS

(75) Inventor: Seiki Takahashi, Iwate Pref. (JP)

(73) Assignee: Iwate University, Iwate Pref. (JP)

( * ) Notice: Subject to any disclaimer, the term of this patent is extended or adjusted under 35 U.S.C. 154(b) by 0 days.

(21) Appl. No.: 09/608,914

(22) Filed: Jun. 30, 2000

(30) Foreign Application Priority Data

Jul. 2, 1999 (JP) .......................................... 11-189269

(51) Int. Cl.$^7$ ................................................. G01B 5/30
(52) U.S. Cl. ........................................... 73/760; 73/779
(58) Field of Search ................................. 73/779, 760

(56) References Cited

U.S. PATENT DOCUMENTS

| | | | | |
|---|---|---|---|---|
| 4,931,729 A | * | 6/1990 | Pratt ............................ | 73/779 |
| 4,931,730 A | * | 6/1990 | Olsen et al. .................. | 73/779 |
| 6,073,493 A | * | 6/2000 | Sakamoto et al. ............. | 73/779 |

* cited by examiner

Primary Examiner—Benjamin R. Fuller
Assistant Examiner—Andre Allen
(74) Attorney, Agent, or Firm—Knobbe, Martens, Olson & Bear, LLP

(57) ABSTRACT

A nondestructive test method determines fatigue of a test ferromagnetic construction material by quantifying a change in effective stress due to aging of the test material, in which the magnetic susceptibility ($\chi_c$) of the test material is measured in its aged state under a magnetic field having a specified intensity (H) according to a relation as expressed by a first equation: $c=\chi_c H^3$. The magnetic susceptibility ($\chi_c$) so measured and the magnetic field intensity (H) are put into the first equation, to obtain a susceptibility coefficient (c) of the test material. The susceptibility coefficient (c) so obtained is put into a second equation: $\sigma=\{\log (c)-a\}/b$, where a and b are known constants determined by an internal structure of the test material, to obtain a current tensile stress ($\sigma$) of the test material. The current tensile stress ($\sigma$) of the test material so obtained is compared with a known, initial tensile stress ($\sigma_0$) of the same test material, to determine a change in effective tensile stress of the test material.

8 Claims, 14 Drawing Sheets

NONDESTRUCTIVE FATIGUE TEST METHOD FOR FERROMAGNETIC CONSTRUCTION MATERIALS

BACKGROUND OF THE INVENTION

1. Field of the Invention

The present invention relates to a nondestructive test method for quantitatively determining fatigue of a ferromagnetic construction material, or of a structure comprised of such a material.

2. Description of the Related Art

Conventional nondestructive test methods for determining fatigue of materials are generally based on investigation of generation and growth of cracks in the material, and thus, it is highly important to find out as minute cracks as possible. With such a conventional nondestructive test method, it is practically impossible to evaluate fatigue of the material before cracks are generated.

There is known another type of nondestructive fatigue test method that is applicable to ferromagnetic construction materials or structures comprised of such a construction material. In this test method, the coercive force and magnetic susceptibility of the test material are measured in the range approaching to saturation. In this instance, for precisely determining the coercive force of the test material, it is necessary to provide a magnetizing yoke and a winding coil around it such that the test material can be magnetized to a saturation level and then demagnetized until the internal magnetic flux becomes zero. To this end, a magnetic force has to be applied that is far larger than the coercive force of that material, by using a large magnetizing yoke and allowing a large magnetizing current to flow through the magnetizing coil. A test machine incorporating such a large magnetic yoke and a large capacity magnetizing power source for energizing the magnetic yoke is not only expensive, but also makes the entire system heavy and large in size to require a noticeable installation space.

SUMMARY OF THE INVENTION

It is therefore a primary object of the present invention to provide an improved test method for nondestructively determining the fatigue of a ferromagnetic construction material, which advantageously eliminates the above-mentioned problems of the prior art.

One aspect of the present invention resides in a method for nondestructively determining fatigue of a test ferromagnetic construction material having a known, initial tensile stress $\sigma_0$, by quantifying a change in effective stress due to aging of the material. The test method according to the present invention comprises the following four steps.

The first step is to measure a magnetic susceptibility $\chi_c$ of the test material in its aged state, under a magnetic field having a predetermined intensity H, according to a relation as expressed by a first equation:

$$c = \chi_c H^3 \quad (1).$$

The second step is to determine a susceptibility coefficient c of the test material by putting the magnetic field intensity H and the measured magnetic susceptibility $\chi_c$ of the test material into the first equation.

The third step is to determine a current tensile stress σ of the test material, by putting the value of the susceptibility coefficient c into a second equation:

$$\sigma = \{\log(c) - a\}b \quad (2)$$

where a and b are known constants determined by a structure of the test material.

Finally, the fourth step is to determine a change in effective tensile stress of the test material, by comparing the current tensile stress σ of the test material with the initial tensile stress $\sigma_0$ of the test material.

Another aspect of the present invention resides in an apparatus nondestructively determining fatigue of a test ferromagnetic construction material having a known, initial tensile stress ($\sigma_0$), by quantifying a change in the effective stress due to aging of the test material. The apparatus according to the present invention comprises:

i) measuring means for measuring the magnetic susceptibility ($\chi_c$) of the test material in its aged state, under a magnetic field of a specified intensity (H), according to a relation as expressed by a first equation:

$$c = \chi_c H^3 \quad (1)$$

ii) stress calculation means for calculating and thereby determining a current tensile stress (σ) of the test material, by determining a susceptibility coefficient (c) of the test material after putting the measured magnetic susceptibility ($\chi_c$) of the test material and the magnetic field intensity (H) into the first equation, and then putting the susceptibility coefficient (c) into the second equation:

$$\sigma = \{\log(c) - a\}/b \quad (2)$$

where a and b are known constants determined by an internal structure of the test material; and iii) evaluation means for determining a change in effective stress of the test material due to aging thereof, by comparing the current tensile stress (σ) of the test material with its initial tensile stress ($\sigma_0$).

The nondestructive test apparatus according to the present invention, as a whole, may be comprised of a personal computer installed with programs based on the algorithm which enables execution of the above steps.

The principle of the present invention will be described below with reference to experimental test data. To elucidate the interrelationship between the mechanical and magnetic properties of steel materials, test materials were prepared which consist of single crystal pure iron, polycrystalline pure iron, and low-alloy steel A533B, respectively. These test materials were formed into samples having shapes as shown in FIGS. 1(a), 1(b) and 1(c), respectively, which are to be subjected to tensile and hysteresis loop tests. The material formed into a sample as shown in FIG. 1(a) was used for the tensile test, while the material for med into a sample as shown in FIG. 1(b) or 1(c) was used for the hysteresis loop test. As for the hysteresis loop test, the polycrystalline pure iron and low-alloy steel A533B took the shape of FIG. 1(b) while the single crystal pure iron took the shape of FIG. 1(c). Table 1 below shows the composition of the low-alloy steel A533B submitted to the test.

TABLE 1

| A533B | C | Si | Mn | P | S | Cu | Ni | Mo | Al |
|---|---|---|---|---|---|---|---|---|---|
| Wt. % | 0.18 | 0.15 | 1.5 | 0.004 | 0.001 | 0.03 | 0.66 | 0.56 | 0.01 |

FIGS. 2 to 4 illustrate the stress-strain characteristics of the test samples, obtained from the tensile test. FIG. 2 represents the results from an Fe since crystal sample, and shows that the strain rate (i.e., extension rate) is 1.5%/min. FIG. 3 represents the results from an Fe polycrystalline sample, and shows that the strain rate is 1.2%/min. FIG. 4 represents the results from an alloy steel A533B sample, and shows that the strain rate is 1.2%/min.

FIGS. 5 and 6 illustrate the magnetization curves obtained from the hysteresis loop test under application of stresses. FIG. 5 shows the hysteresis loop characteristics of an Fe single crystal sample with plastic deformation under a stress (0 MPa, 55 MPa, or 115 MPa), while FIG. 6 shows the hysteresis loop characteristics of an Fe polycrystalline sample with plastic deformation under a stress (0 MPa, 550 MPa, or 663 MPa). The stresses applied were chosen to be equal to 0 MPa and the stress that develops just before breakage, both of which had been obtained from a preparatory tensile test, and to intermediate values between these two values.

From the gradient of the magnetization curve of a test material as depicted in FIGS. 5 and 6, it is possible to determine the magnetization susceptibility $\chi_c$ of the test material at a magnetic field intensity exceeding its coercive force. FIG. 7 illustrates the relationship of the magnetic susceptibility of the low-alloy steel A533B with the magnetic field intensity H above the coercive force of the material obtained from the magnetization curve under a stress of 663 MPa as depicted in FIG. 6. Similarly, FIG. 8 illustrates the relationship of the logarithmic magnetic susceptibility (log $\chi_c$) of the low-alloy steel A533B with the logarithmic magnetic field intensity H (log H) obtained from the magnetic susceptibility curve $\chi_c$ which changes as a function of the magnetic field intensity H under the stress of 663 MPa as depicted in FIG. 7. Finally, FIG. 9 illustrates the relationship of the logarithmic magnetic susceptibility (log $\chi_c$) of an Fe single crystal material with the logarithmic magnetic field intensity H (log H) under the stress of 115 MPa. The straight line indicates the relation between the magnetic susceptibility $\chi_c$ and the magnetic field intensity H in the equation (1).

From the curves in FIGS. 8 and 9, the following equation (3) can be obtained:

$$\log \chi_c = -3 \log H + A \tag{3},$$

where A is a constant. The equation (3) can be transformed into the following equation (4):

$$\chi_c = c/H^3 \tag{4}.$$

It is noted that the equation (4) is equivalent to the equation (1) explained above.

In the equation (1) or (4), the factor c is a parameter representing a state of material that is determined by dislocations or other lattice defects, and grain boundaries existent in the same material, and defined as the "susceptibility coefficient". Existence of such susceptibility coefficient c has been known through tests where a magnetic field having a strong intensity is applied to a single crystal material. However, experiments performed by the inventors revealed for the first time that the susceptibility coefficient c exists also in single crystal pure iron, polycrystalline pure iron and low-alloy steel which are exposed to a magnetic field having a relatively low intensity.

With the equation (1): $c = \chi_c H^3$ obtained from the hysteresis of the test materials subjected to the hysteresis loop test, it is possible to plot the susceptibility coefficient c of the materials as a function of the intensity of a magnetic field above the coercive force of the materials, and to further plot the logarithmic values of c as a function of the applied stresses, which gives the results as shown in FIG. 10. The solid triangles (▲), solid circles (●) and solid diamonds (♦) represent the results obtained from an Fe single crystal material, an Fe polycrystalline material, and a low-alloy steel material, respectively. It has been revealed as a result of investigations by the inventors, that the relation of susceptibility coefficient c with stress σ can be expressed by a single equation (5):

$$\sigma = \{\log (c) - a\}/b \tag{5},$$

where a and b are constants determined by the internal, crystal structure of the test material. The single crystal pure iron, polycrystalline pure iron, and low-alloy A533B steel submitted to the test each has a body-centered cubic (BCC) lattice structure, and contains iron atoms as main ingredient. Thus, the characteristic under study observed among those materials can be represented by a single line as shown in FIG. 10 which is expressed by the equation (5).

Therefore, even for a sample whose stress is unknown, it is possible to nondestructively determine the current stress σ by resorting to the hysteresis loop test, after determining the susceptibility coefficient c and putting the result into the equation (5). The stress σ serves as a parameter representing the mechanical strength of the material.

It is possible to determine the susceptibility coefficient c of a test material by using a magnetic yoke or winding coil and by nondestructively measuring its hysteresis characteristics. Since what is necessary in this test is only to determine the magnetic susceptibility of the material, it is possible to reduce the intensity of magnetic field to a far lower level than is required in the conventional test based on the measurement of a coercive force, and hence to reduce the magnetizing current to a far lower level than is required in such a conventional test.

Therefore, with the method according to the present invention, it is possible to precisely determine the current stress of a test material by exposing it to a magnetic field with a far less intensity than is required for the conventional method, and thereby nondestructively determine fatigue of the test material. It is to be noted that when a construction material is aged, i.e., exposed to a stress over a long period, internal lattice defects and dislocations develop; microscopic structures within the material to sustain internal stresses decrease; and the effective stress of the material increases. In this context, the increased effective stress of the test material in its aged state is the current stress of that material.

Moreover, whereas the conventional fatigue test method based on the relation between the coercive force and the effective tensile stress allows the maximum of the applied tensions to be only several to several tens times of the minimum, the test method according to the present invention determines fatigue of a test material based on the relation between the susceptibility coefficient c and the current stress σ, allowing the maximum stress σ to be about 3000 times of the minimum, as seen from FIG. 10. This indicates that the method according to the present invention is more significantly sensitive to change in the tensile stress, which serves as a parameter for evaluating fatigue of a test material.

Incidentally, since it is known that there exists a simple relation between stress and the dislocation density of a material, it is possible roughly to estimate the dislocation density of the material from the tensile stress, to thereby nondestructively determine one of the factors representing fatigue of the material.

The method according to the present invention can be applied not only to ferromagnetic construction materials having a single crystal structure, but also to ferromagnetic construction materials having a polycrystalline structure, and to low-alloy steel. The present invention provides a highly sensitive, nondestructive test method for determining fatigue of ferromagnetic construction materials, which makes it readily possible to nondestructively determine the dislocation density of a ferromagnetic construction material and its distribution within the material even before cracks are generated in the material, and also to perform nondestructive measurement using only a small magnetic yoke and a small capacity power source.

In the nondestructive test method according to the present invention, the initial tensile stress $\sigma_0$ of the test material may be obtained from the following equation:

$$\sigma_0 = F/S \qquad (6)$$

where F represents a force applied to the test ferromagnetic construction material, and S the sectional area of the material normal to the direction of the force. In this instance, assuming that the external force and/or the internal force applied to the test material are known, the initial tensile stress $\sigma_0$ can be readily derived from the equation (6).

Alternatively, the initial tensile stress $\sigma_0$ of the test material may be obtained from the equations (1) and (2) in the same manner as is in the current tensile stress σ. In this instance, even when the external force and/or the internal force applied to the test material are unknown, the initial tensile stress $\sigma_0$ can be readily derived as is the case with the current tensile stress σ.

Still further, in the nondestructive test method according to the present invention, there may be used a U-shaped magnetic yoke for measuring the intensity H of a magnetic field applied to a test ferromagnetic construction material. It is then possible to perform a nondestructive measurement on the test material having a shape which does not readily permit a coil to be wound around it.

DESCRIPTION OF THE PREFERRED EMBODIMENTS

Figure 11:
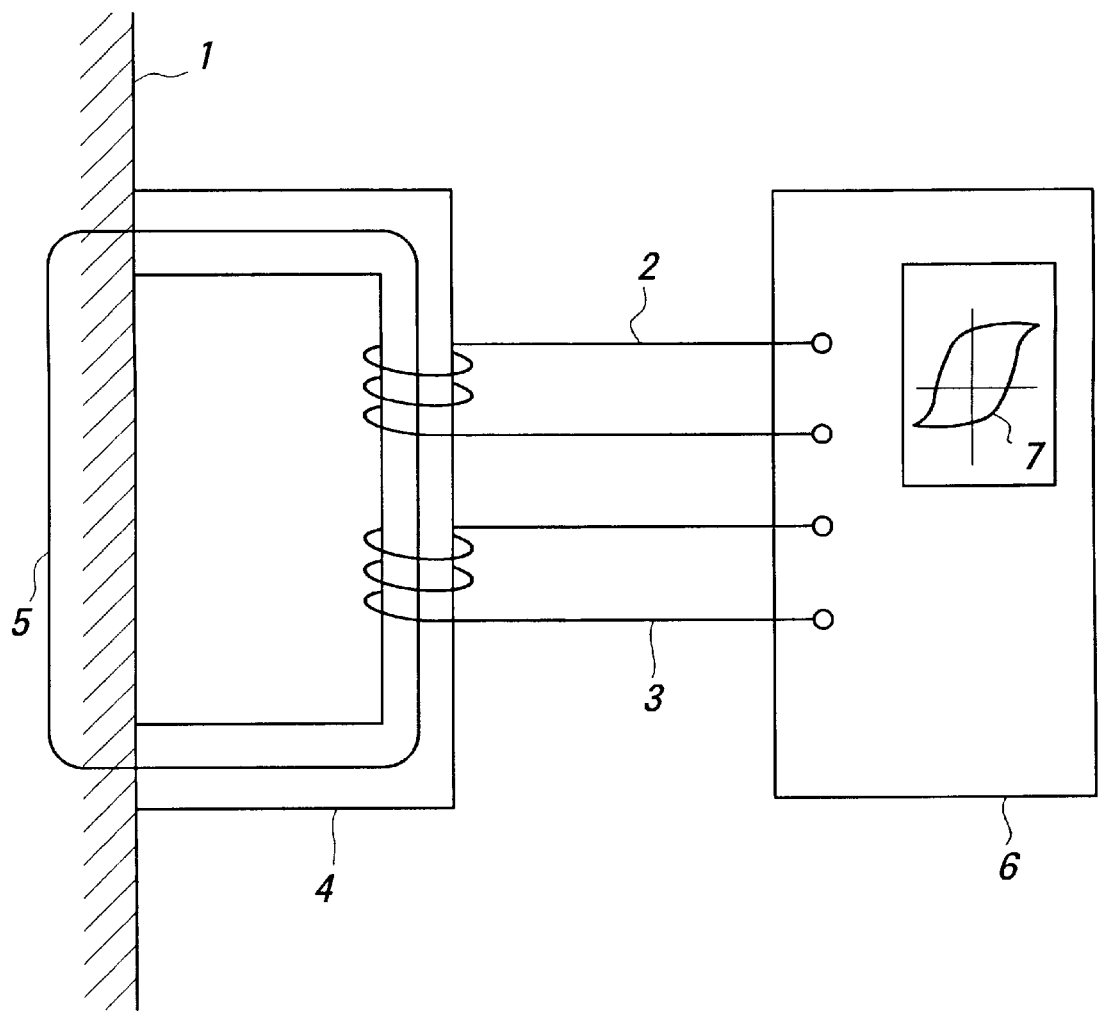
FIG. 11 is a schematic view showing one embodiment of the nondestructive fatigue test method according to the present invention as applied to determine fatigue of a ferromagnetic construction material.

The present invention will be described below in further detail, with reference to preferred embodiments shown in the attached drawings. FIG. 11 illustrates a first example of the nondestructive fatigue test method according to the present invention, wherein reference numeral 1 denotes a test structure comprised of a ferromagnetic construction material and exposed to external and/or internal forces; 2 a magnetizing coil; 3 a flux detecting coil; and 4 a magnetic yoke on which these coils 2, 3 are wound. As shown in FIG. 11, the test structure 1 has a shape for which a direct winding of the coils 2, 3 is impossible. Thus, the magnetic yoke 4 incorporating the magnetizing coil 2 and flux detecting coil 3 is tightly applied onto the test structure 1 to form a closed magnetic circuit 5. The magnetizing coil 2 and flux detecting coil 3 are connected to a magnetization measuring device 6. The magnetization measuring device 6 may be one which is commercially available in the market. Curves 7 represent the magnetization or hysteresis loop of the test structure 1, which is determined by, and displayed on the magnetization measuring device 6.

In the test method according to the present invention, in order to perform a nondestructive fatigue test of the structure 1, the magnetization measuring device 6 supplies the magnetizing coil 2 with a magnetizing current. As a result, a voltage is induced in the flux detecting coil 3 and transmitted to the magnetization measuring device 6. The voltage is amplified and integrated by the measuring device 6 to determine the hysteresis loop 7 of the test structure 1. In this example, it is only necessary to determine the magnetic susceptibility $\chi_c$ of the test structure. Therefore, the measurement can be performed at a magnetic field whose intensity H is as low as 60 Oe. Such a low intensity is in a clear contrast to 1000–2000 Oe which is required in the conventional test method wherein the test structure has to be magnetized to a saturation level.

The hysteresis loop obtained from the test structure exposed to a magnetic field of a low intensity H may contain errors due to the three dimensional expanse of the flux pathways in the ferromagnetic material of the test structure 1 and also due to the demagnetizing factor. To obtain the hysteresis loop characteristic free from such errors, it is necessary to determine a correction factor. Such a correction factor might be obtained by a computer experiment based on a known static magnetic field analysis, or by a mock-up experiment simulating the measurement system.

With simulated hysteresis loop characteristics obtained under a magnetic field of the low intensity H as explained above, the magnetic susceptibility $\chi_c$ of the test material under the magnetic field intensity H is measured. The susceptibility coefficient c of the test material is determined according to the relation between the magnetic susceptibility $\chi_c$ and the magnetic field intensity H as expressed by the equation (1):

$$c = \chi_c H^3 \quad (1)$$

Then, the effective tensile stress $\sigma$ within the test material exposed to external and/or internal forces is determined by putting the susceptibility coefficient c into the equation (2):

$$\sigma = \{\log (c) - a\}/b \quad (2)$$

in which a and b are known constants determined by the internal structure of the material.

Figure 12:
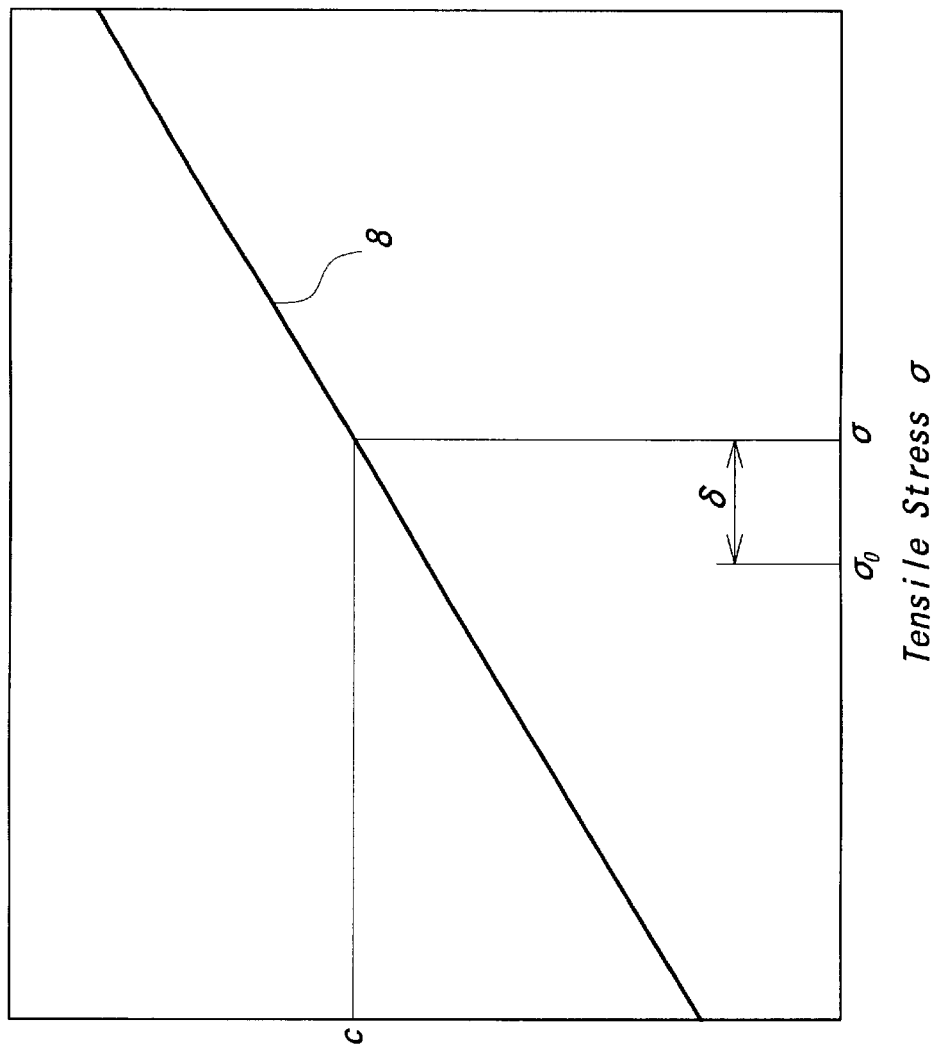
FIG. 12 is a graph which is used to determine the fatigue in the structure comprised of a ferromagnetic construction material, based on effective tensile stress σ as computed from the susceptibility coefficient c.

The constants a and b in the equation (2) may be determined in advance by a preparatory test with respect to a test piece which is made of the same ferromagnetic material. When the values of a and b are put into the equation (2), the relation of the susceptibility coefficient c with the tensile stress $\sigma$ is represented by a substantially straight calibration line 8 in FIG. 12. The effective tensile stress $\sigma$ of the test material corresponding to the susceptibility coefficient c can be readily determined from the calibration line 8.

It is necessary to determine the initial tensile stress $\sigma_0$ of the test ferromagnetic structure 1 at the initial phase because it serves as a reference for determining the current fatigue of the test material after it has been aged. When the direction and magnitude of the force applied to the ferromagnetic structure 1 are known, the initial tensile stress $\sigma_0$ can be obtained from the equation (3):

$$\sigma_0 = F/S \quad (3)$$

where F represents the intensity of the force, and S the sectional area of the test structure normal to the direction of the force.

On the contrary, when the direction and/or the magnitude of the force applied to the test structure 1 are unknown, it is still possible to determine the initial tensile stress $\sigma_0$ of the structure by using the above-mentioned equations (1) and (2) as in the case of the effective tensile stress $\sigma$.

The currently effective tensile stress $\sigma$ obtained as above is compared with the initial tensile stress $\sigma_0$, and the difference $\delta$ between these stresses is used as a parameter which represents the fatigue of the test structure 1. It is thus possible to nondestructively determine the fatigue of a structure which is comprised of a ferromagnetic material.

Figure 1A:
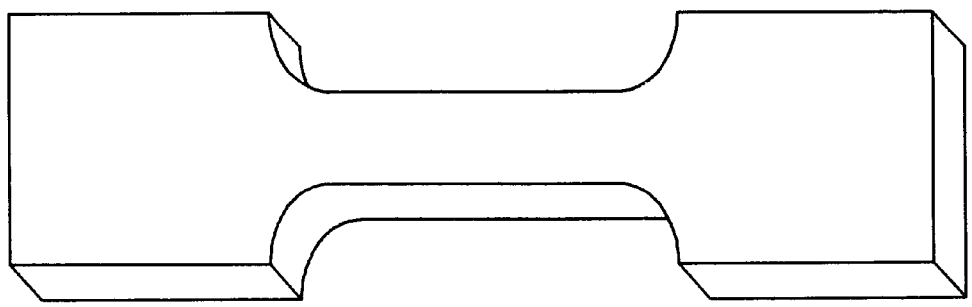
FIGS. 1a, 1b and 1c are views showing the shape of samples to be submitted to the tensile and hysteresis loop tests.
Figure 1B:
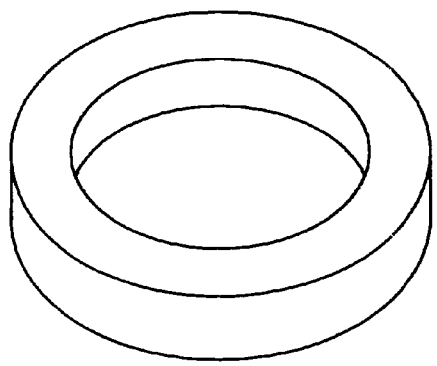
Figure 1C:
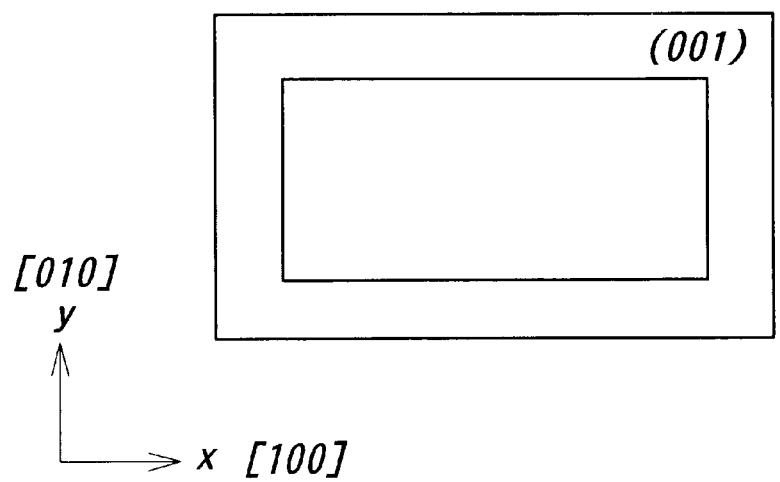
Figure 2:
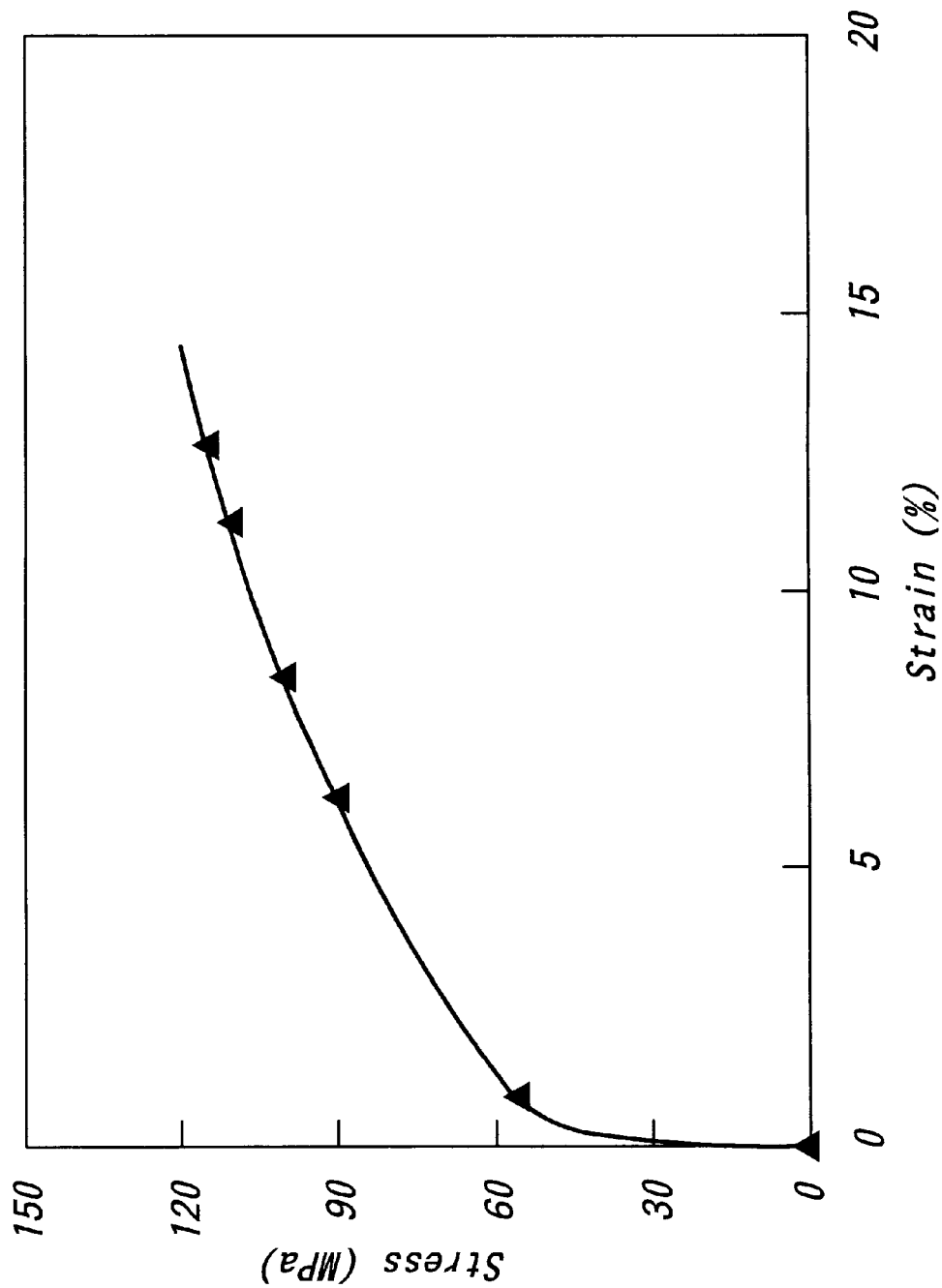
FIG. 2 is a stress-strain diagram of a single crystal pure iron sample obtained from the tensile test.
Figure 3:
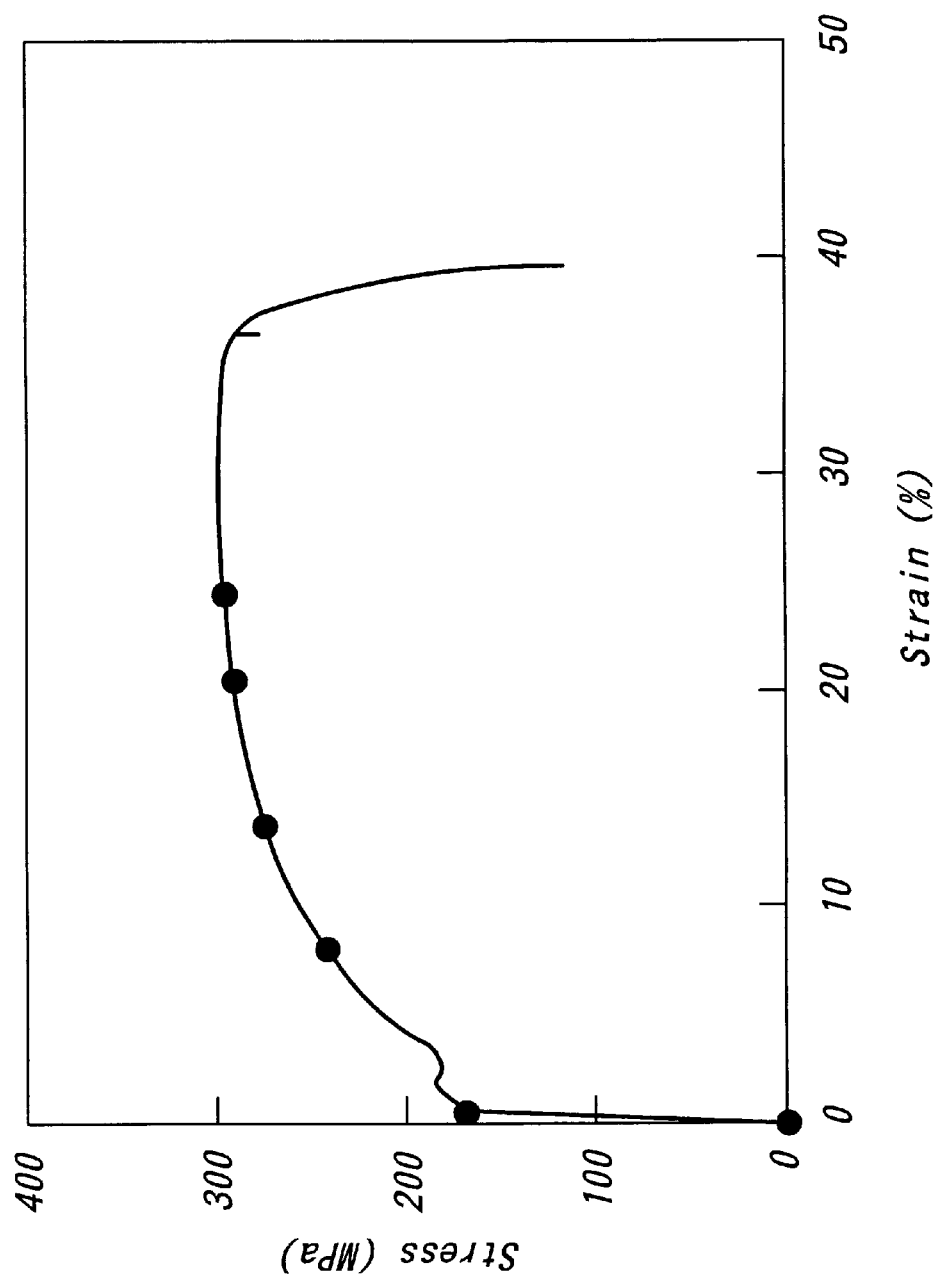
FIG. 3 is a stress-strain diagram of polycrystalline pure iron sample obtained from the tensile test.
Figure 4:
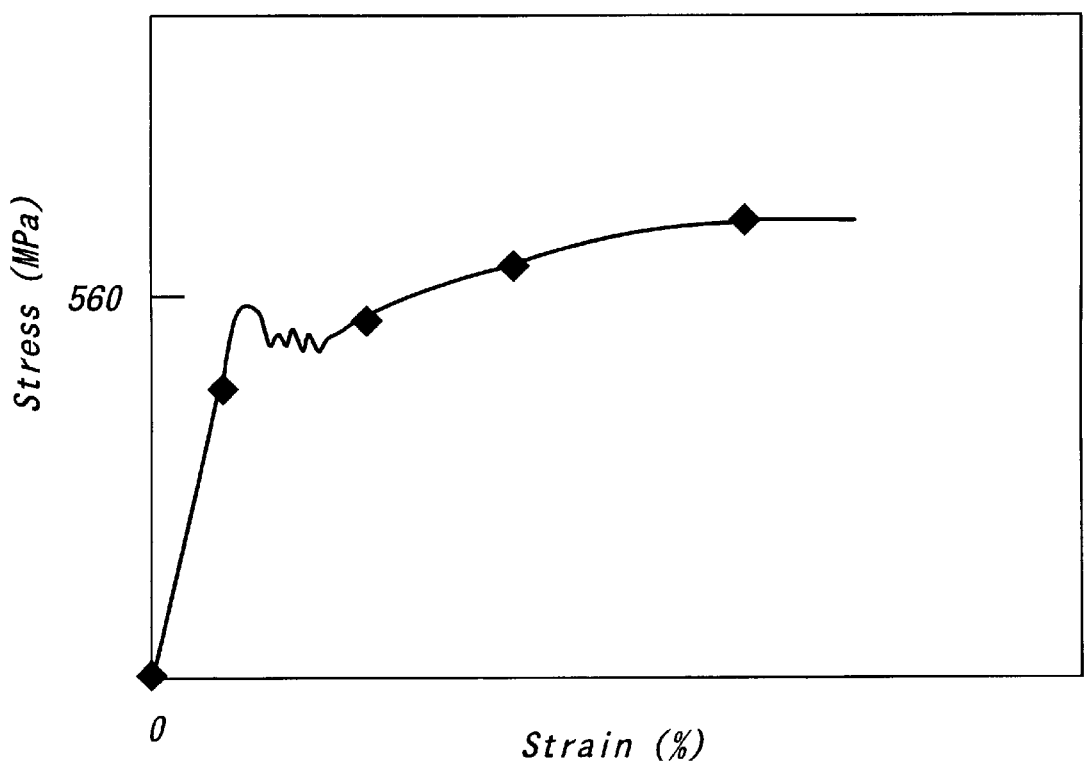
FIG. 4 is a stress-strain diagram of a low-alloy steel A533B sample obtained from the tensile test.
Figure 5:
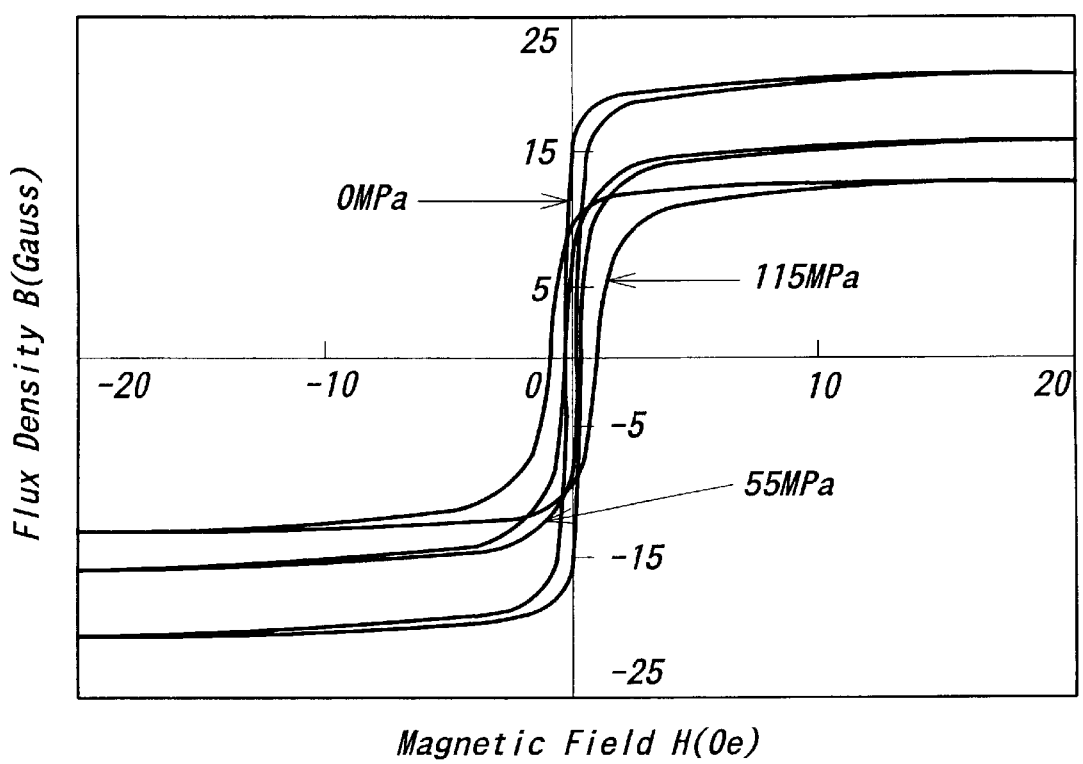
FIG. 5 is a graph showing the hysteresis characteristics of Fe single crystal samples under the stresses of 0 MPa, 55 MPa and 115 MPa, respectively.
Figure 6:
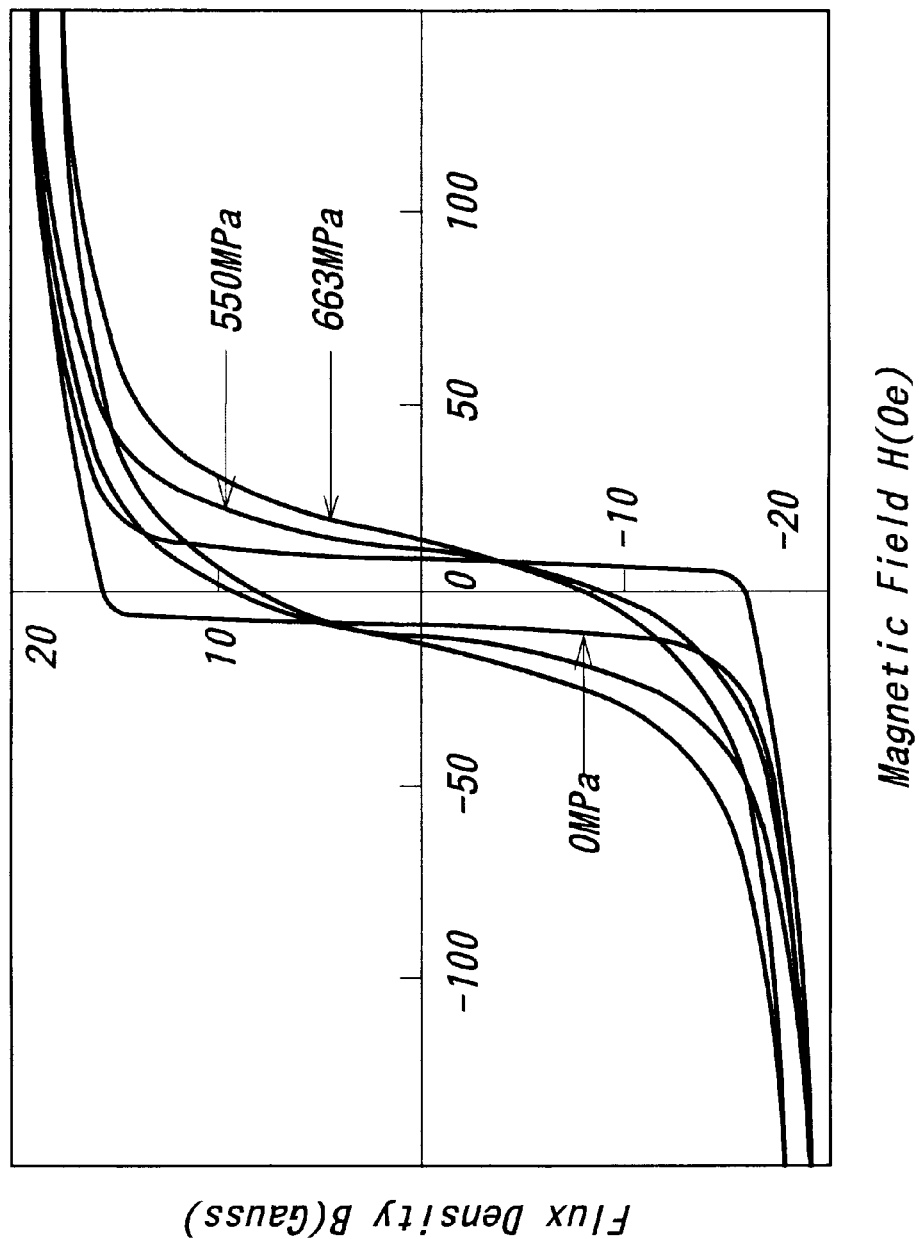
FIG. 6 is a graph showing the hysteresis characteristics of low-alloy steel A533B samples under the stresses of 0 MPa, 550 MPa and 633 MPa, respectively.
Figure 7:
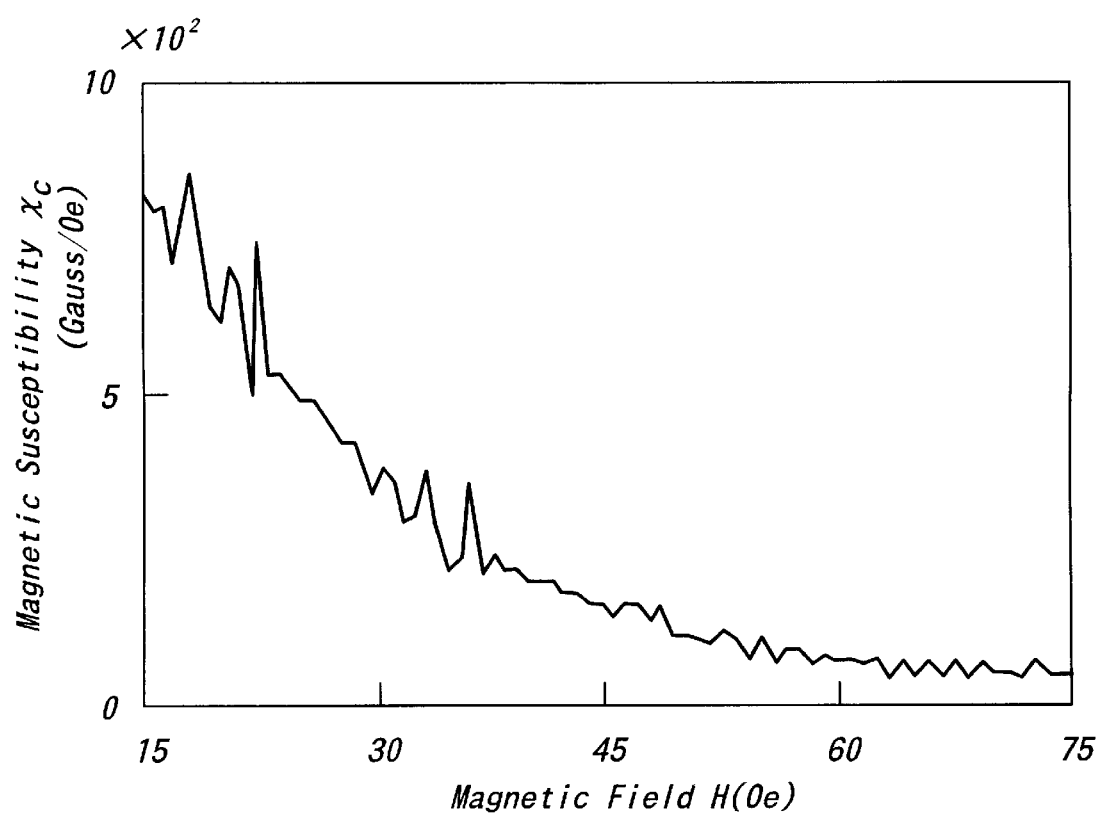
FIG. 7 is a graph showing the relation of the magnetic susceptibility $\chi_c$ of a low-alloy steel A533B sample under the stress of 663 MPa, with the intensity H of the magnetic field.
Figure 8:
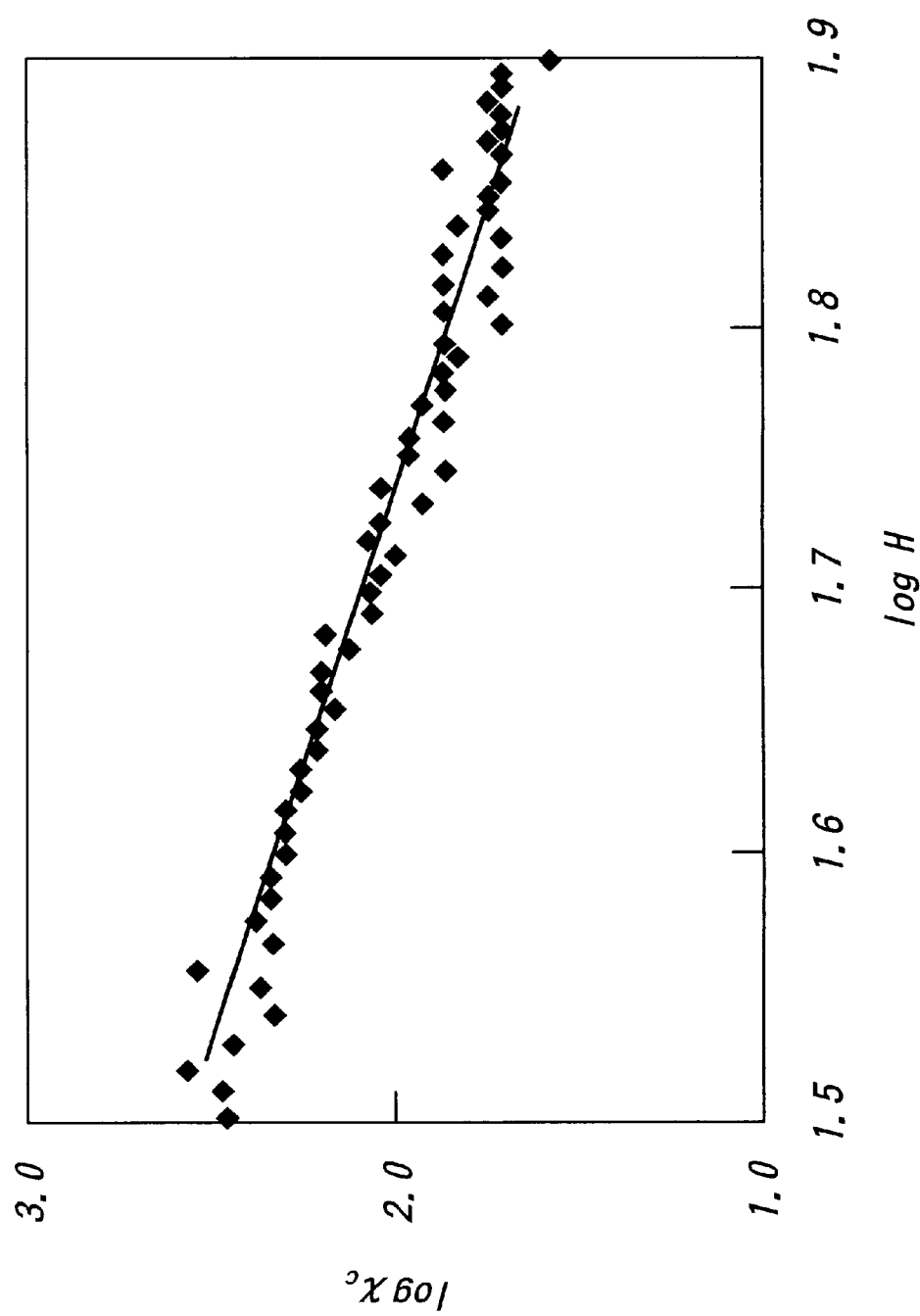
FIG. 8 is a graph showing the relation of the logarithmic value $\log \chi_c$ of the magnetic susceptibility $\chi_c$ of a sample of the low-alloy steel A533B under the stress of 663 MPa, with the logarithmic value log H of the magnetic field intensity H.
Figure 9:
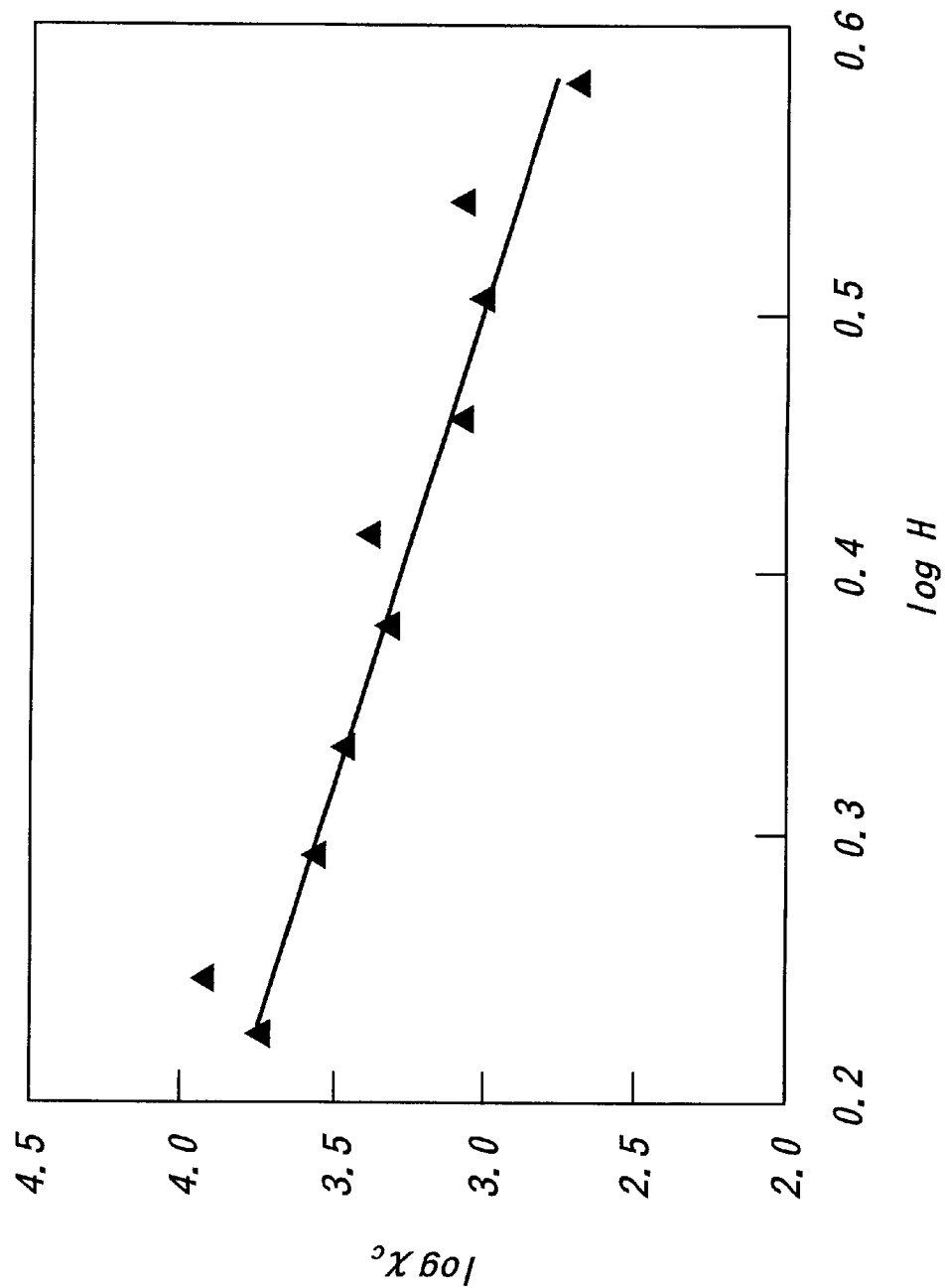
FIG. 9 is a graph showing the relation of the logarithmic values $\log \chi_c$ of the magnetic susceptibility $\chi_c$ of a Fe single crystal sample under the stress of 115 MPa, with the logarithmic value log H of the magnetic field intensity H.
Figure 10:
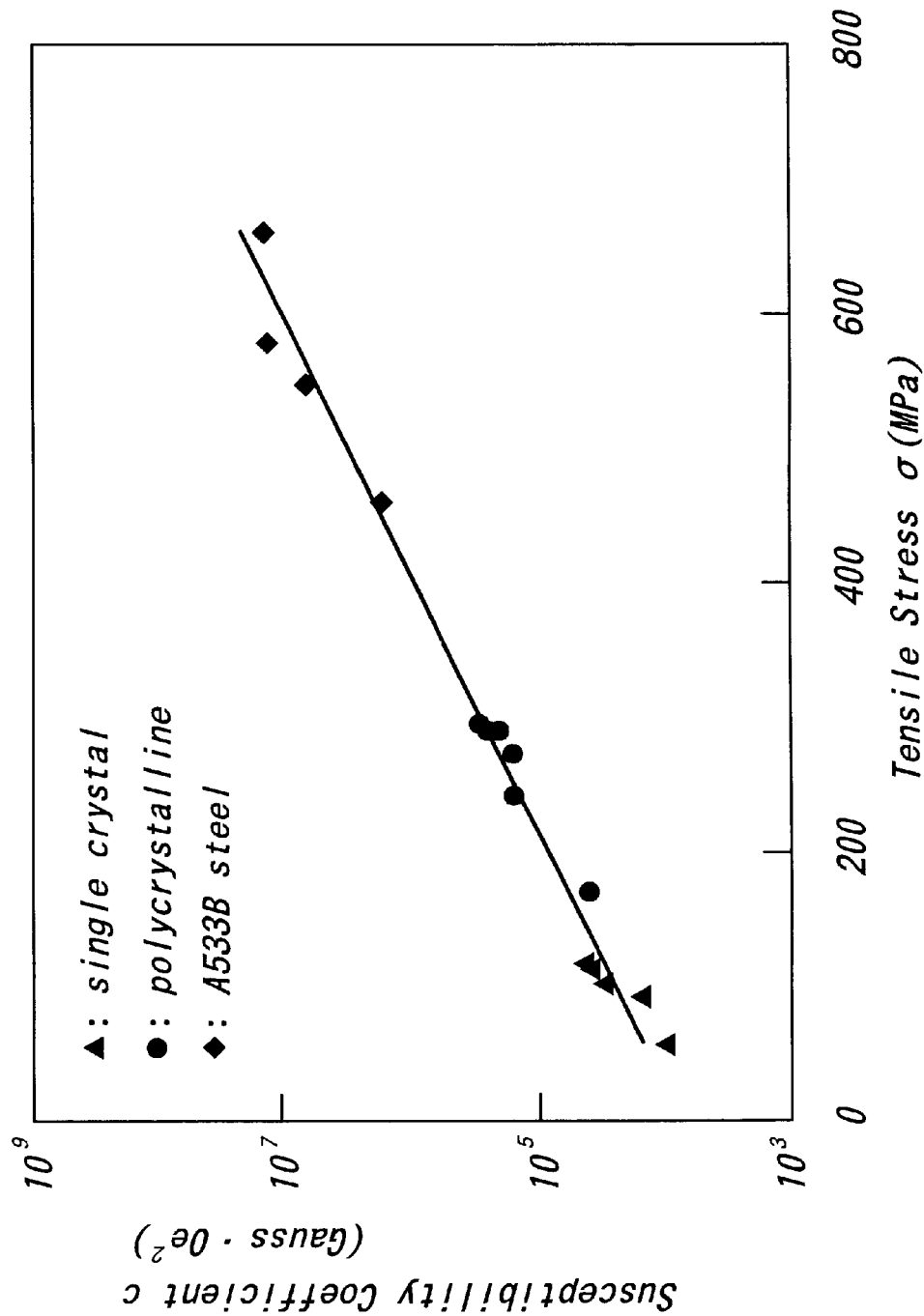
FIG. 10 is a graph obtained by experiments and showing the relation of the susceptibility coefficient c of the test samples with the tensile stress σ.

Therefore, the nondestructive fatigue test method according to the illustrated embodiment makes it possible (i) to obtain a hysteresis curve under a magnetic field of a far lower intensity than is required for the conventional method, (ii) to calculate the susceptibility coefficient c therefrom, to precisely and nondestructively determine the effective tensile stress $\sigma$ corresponding to the above susceptibility coefficient c on the calibration line 8 which represents the relation of the susceptibility coefficient with the tensile stress as depicted in FIG. 8, (iii) to compare the current stress with the initial stress, and (iv) to nondestructively determine the fatigue of the test material. Further, because the test method is applicable not only to single crystal ferromagnetic construction materials but also to polycrystalline ferromagnetic construction materials and low-alloy steel, it is possible to precisely and nondestructively determine the fatigue of any structure made of a ferromagnetic construction material, such as a pressure vessel of a nuclear reactor, before cracks are actually generated in the structure, by determining the density and distribution of dislocations, with a simple apparatus incorporating a small magnetic yoke and a small capacity magnetizing power source.

Figure 13:
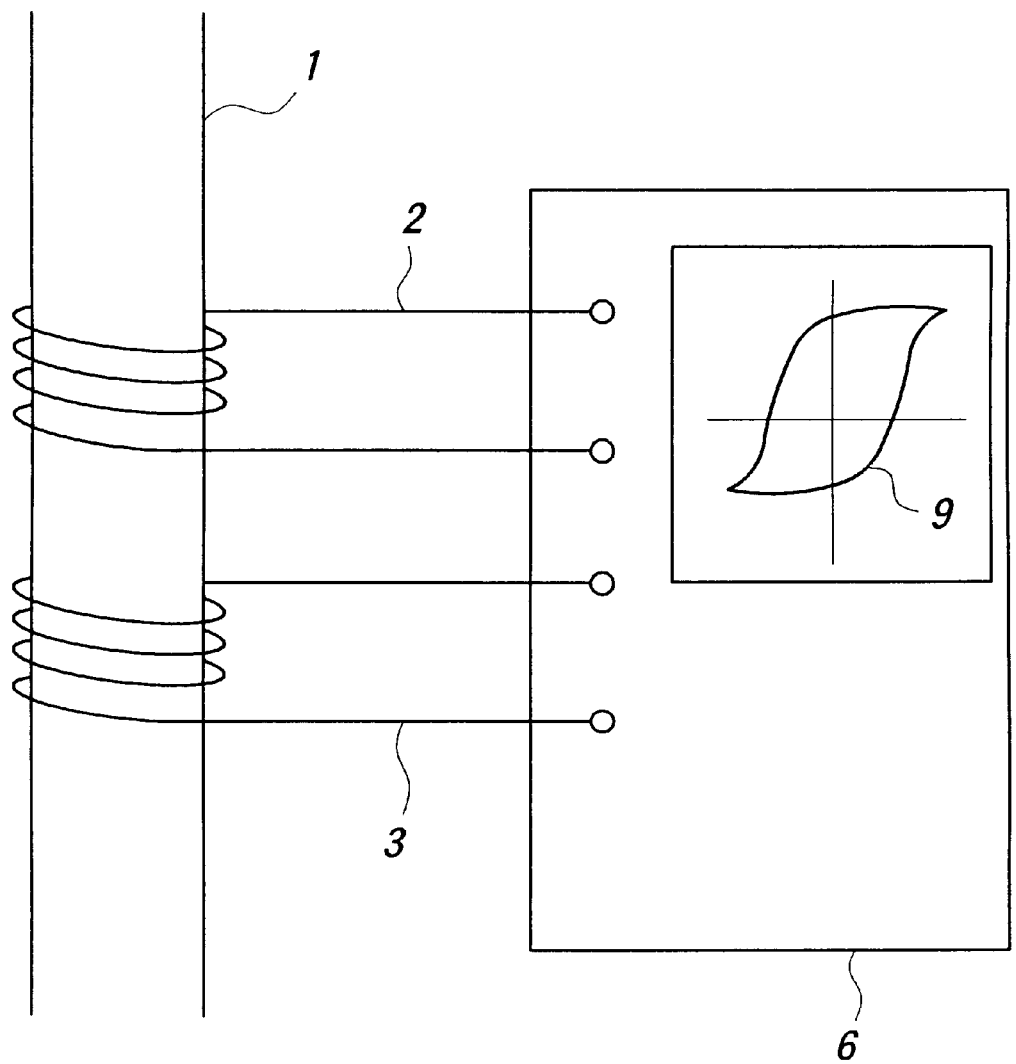
FIG. 13 is a schematic view showing another embodiment of the nondestructive fatigue test method according to the present invention as applied to determine fatigue of a ferromagnetic construction material.

FIG. 13 illustrates a second embodiment of the nondestructive fatigue test method according to the present invention which is also applied to determine the fatigue of a ferromagnetic construction material. In contrast to the above-mentioned first embodiment, the test structure 1 in the present embodiment has a shape which allows a magnetizing coil 2 and a flux detecting coil 3 to be directly wound thereon. Thus, the magnetizing coil 2 and the flux detecting coil 3 are wound on the test structure 1 and connected to the hysteresis loop determining device 6 which may be comprised of a commercially available products as in the first embodiment. The curve 9 represents the magnetization or the hysteresis loop of the test structure 1 which is determined by, and displayed on the hysteresis loop determining device 6 as a result of the test performed.

The second embodiment shown in FIG. 13 is similar to the first embodiment in that the susceptibility coefficient c is calculated from the hysteresis characteristic 9 obtained from a measurement performed under a magnetic field of a very low intensity, and the effective tensile stress $\sigma$ is obtained from the susceptibility coefficient c. Then, the currently effective tensile stress $\sigma$ of the test structure 1 is compared with its initial tensile stress $\sigma_0$, and the difference $\delta$ between these stresses is used to nondestructively determine the fatigue of the test structure.

The nondestructive fatigue test method according to the second embodiment explained above achieves all of the functional advantages (i) through (iv) of the first embodiment. Additionally, the test method of the second embodiment makes it possible nondestructively to determine the fatigue of a ferromagnetic construction material without requiring a magnetic yoke, thereby making the entire system further simple in structure and light in weight.

Figure 14:
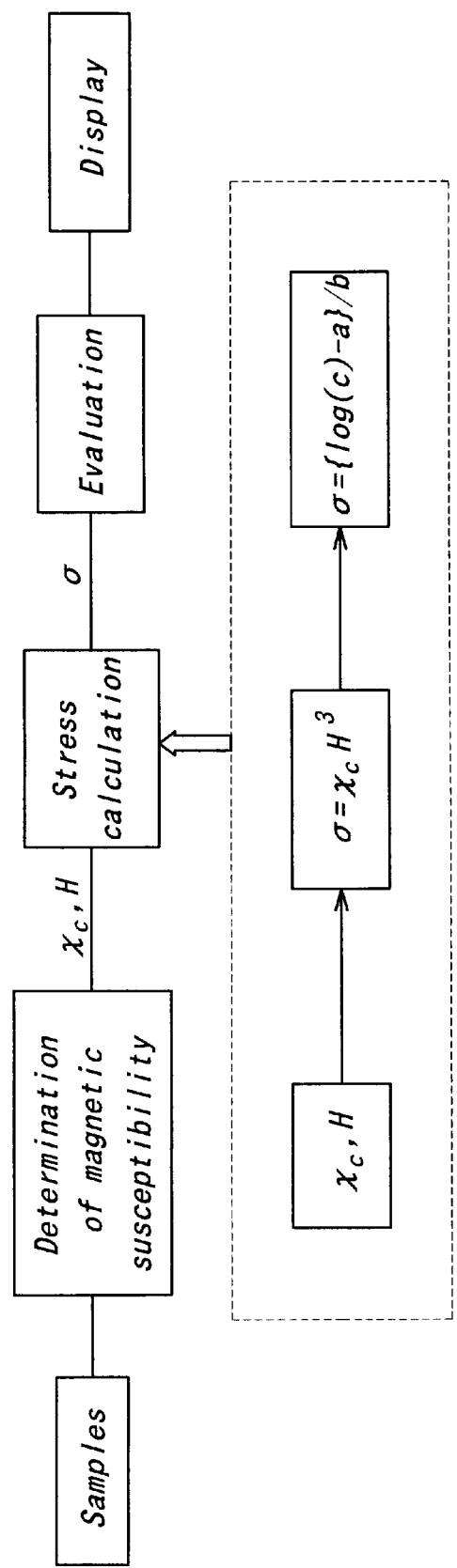
FIG. 14 is a block diagram showing the basic algorithm performed by the apparatus according to the present invention.

The basic algorithm performed in the test method according to the present invention is schematically shown in FIG. 14. The test apparatus suitable for carrying out the test method according to the present invention may be comprised of an appropriate work station or a personal computer incorporating programs based on the algorithms which is so prepared as to execute the above process steps.

While the present invention has been fully described above with reference to specific embodiments, they were presented solely for the purpose of illustration. Thus, a skilled person will readily appreciate that various changes or modifications may be made without departing from the scope of the invention as defined by the appended claims.

What is claimed is:

1. A method for nondestructively determining fatigue of a test ferromagnetic construction material having a known, initial tensile stress ($\sigma_0$), by quantifying a change in effective stress due to aging of the material, said method comprising the steps of:

measuring a magnetic susceptibility ($\chi_c$) of the test material in an aged state thereof, under a magnetic field having a predetermined intensity (H), according to a relation as expressed by a first equation:

$$c = \chi_c H^3;$$

determining a susceptibility coefficient (c) of the test material, by putting the magnetic field intensity (H) and the measured magnetic susceptibility ($\chi_c$) of the test material into the first equation;

determining a current tensile stress ((T) of the test material, by putting the so-determined susceptibility coefficient (c) into a second equation:

$$\sigma = \{\log(c) - a\}/b$$

where a and b are known constants determined by an internal structure of the test material; and comparing the current tensile stress ($\sigma$) of the test material with said initial tensile stress ($\sigma_0$), so as to determine a change in effective tensile stress of the test material.

2. The test method according to claim 1, wherein said initial tensile stress ($\sigma_0$) of the test material is determined by putting a force (F) applied to the ferromagnetic construction material and a sectional area (S) of the test material normal to a direction in which the force is applied, into a third equation:

$$\sigma_0 = F/S.$$

3. The test method according to claim 1, wherein said initial tensile stress ($\sigma_0$) of the test material is determined in a manner same as that of the current tensile stress ($\sigma$) of the test material, by using said first and second equations.

4. The test method according to claim 1, wherein the intensity H of the magnetic field applied to the test ferromagnetic construction material is measured by using a magnetic yoke.

5. An apparatus nondestructively determining fatigue of a test ferromagnetic construction material having a known, initial tensile stress ($\sigma_0$), by quantifying a change in effective stress due to aging of the test material, said apparatus comprising:

measuring means for measuring the magnetic susceptibility ($\chi_c$) of the test material in an aged state thereof, under a magnetic field of a specified intensity (H) according to a relation as expressed by a first equation:

$$c = \chi_c H^3;$$

stress calculation means for calculating and thereby determining a current tensile stress ($\sigma$) of the test material, by determining a susceptibility coefficient (c) of the test material after putting the measured magnetic susceptibility ($\chi_c$) of the test material and the magnetic field intensity (H) into the first equation, and putting the susceptibility coefficient (c) into a second equation:

$$\sigma = \{\log(c) - a\}/b$$

where a and b are known constants determined by an internal structure of the test material; and evaluation means for determining a change in effective stress of the test material due to aging thereof, by comparing the current tensile stress ($\sigma$) of the test material with its initial tensile stress ($\sigma_0$).

6. The apparatus according to claim 5, further comprising a magnetic yoke for measuring the intensity H of the magnetic field applied to the test material.

7. The test method according to claim 2, wherein the intensity H of file magnetic field applied to the test ferromagnetic construction material is measured by using a magnetic yoke.

8. The test method according of claim 3, wherein the intensity H of the magnetic field applied to the test ferromagnetic construction material is measured by using a magnetic yoke.

* * * * *